(12) United States Patent
O'Dea

(10) Patent No.: US 6,647,984 B1
(45) Date of Patent: Nov. 18, 2003

(54) APPARATUS FOR CONTROLLING CUFF PRESSURE IN AN ENDOTRACHEAL TUBE

(75) Inventor: John O'Dea, Galway (IE)

(73) Assignee: Caradyne (R&D) Limited, Galway (IE)

( * ) Notice: Subject to any disclaimer, the term of this patent is extended or adjusted under 35 U.S.C. 154(b) by 0 days.

(21) Appl. No.: 10/019,547

(22) PCT Filed: Jun. 23, 2000

(86) PCT No.: PCT/IE00/00082
§ 371 (c)(1),
(2), (4) Date: May 15, 2002

(87) PCT Pub. No.: WO01/00267
PCT Pub. Date: Jan. 4, 2001

(30) Foreign Application Priority Data

Jun. 24, 1999 (IE) .............................................. S990525

(51) Int. Cl.$^7$ ................................................ A62B 9/06
(52) U.S. Cl. .............................. 128/207.16; 604/99.02; 128/207.15
(58) Field of Search .............. 604/96.01, 97.01–100.03; 606/191–200; 600/201, 204, 207, 210; 128/200.24, 203.12, 203.14, 204.18, 204.21, 204.23, 205.14, 205.18, 205.24, 207.14–207.18

(56) References Cited

U.S. PATENT DOCUMENTS

| | | | |
|---|---|---|---|
| 4,178,940 A | * | 12/1979 | Au ........................ 128/207.15 |
| 4,471,775 A | | 9/1984 | Clair et al. |
| 4,825,862 A | | 5/1989 | Sato et al. |
| 4,850,349 A | | 7/1989 | Farahany |
| 4,924,862 A | * | 5/1990 | Levinson ............... 128/207.16 |
| 5,235,973 A | | 8/1993 | Levinson |
| 5,487,383 A | * | 1/1996 | Levinson ............... 128/207.15 |
| 5,582,167 A | | 12/1996 | Joseph |
| 5,819,723 A | * | 10/1998 | Joseph .................. 128/207.14 |

FOREIGN PATENT DOCUMENTS

WO    WO 92/03176    3/1992

* cited by examiner

Primary Examiner—Glenn K. Dawson
(74) Attorney, Agent, or Firm—Swanson & Bratschun, LLC (57) ABSTRACT

Apparatus (1) for controlling pressure in a cuff (2) of an endotracheal tube (3) a pole mountable housing (25) within which an inflating medium supply pump (30) is located for supplying inflating medium to the cuff through a communicating tube (18) integral with the endotracheal tube (3) and a delivery tube (37) from the apparatus (1). A pressure transducer (28) connected to the endotracheal tube (3) by a connecting tube (29) monitors the pressure of the ventilating medium in the endotracheal tube (3) for determining transitions from the inspiratory to the expiratory phases of a breathing cycle. A microcontroller (27) controls the supply pump (30) for supplying the inflating medium to the cuff (2) at a first pressure level during the inspiratory phase of each breathing cycle and at a lower second pressure level during the expiratory phase of each breathing cycle.

19 Claims, 3 Drawing Sheets

APPARATUS FOR CONTROLLING CUFF PRESSURE IN AN ENDOTRACHEAL TUBE

The present invention relates to apparatus for controlling cuff pressure in an endotracheal tube.

Endotracheal tubes are well known. In use, an endotracheal tube is inserted through the mouth of a subject into the trachea for facilitating ventilating of the subject from a ventilator or other suitable ventilating medium source. Typically, an endotracheal tube terminates at one end in a coupling for coupling the tube to a supply tube which supplies the ventilating medium source. A inflatable cuff is provided at the other end of the endotracheal tube and extends around the tube so that on inflating of the cuff the endotracheal tube is secured in the trachea of the subject and leak passed of the ventilating medium into the mouth of the subject is avoided during the inrspiratory phase of each breathing cycle. A communicating tube is provided on the endotracheal tube for communicating with the cuff and for facilitating inflating of the cuff. Typically, the communicating tube extends along the side of the endotracheal tube, and ideally, forms an integral part therewith. Typically, the cuff is manually inflated by a syringe to a pressure which is adequate for retaining the endotracheal tube in the trachea and also for preventing leak passed of the ventilating medium. However, care is required in order to avoid over-inflating the cuff, which could lead to injury and trauma, and in particular, to damage of the vocal cords of the subject.

Due to pressure variation of the ventilating medium during a breathing cycle, for example, the pressure variation as a breathing cycle transitions between the inspiratory phase and the expiratory phase, and indeed, over a series of breathing cycles, it is difficult to achieve an adequate degree of sealing of the endotracheal tube between the cuff and the trachea for all such pressure variations to avoid leakage of the ventilating medium into the mouth of the subject.

Additionally, in order to facilitate manual inflating of the cuff by a syringe which can deliver a relatively large volume of air at a relatively low pressure, it is necessary in general to form the cuff from a relatively highly compliant material, for example, a latex material which will inflate at relatively low pressures. However, latex materials suffer from a number of disadvantages. Firstly, latex materials cause allergies in many people, secondly, latex materials tend to be permeable to some of the anaesthetic gases, such as nitrous oxide which can permeate into the cuff. Since the latex material is a highly compliant material, as the nitrous oxide permeates into the cuff the cuff further inflates, and this can cause trauma and indeed, serious injurious effects to the subject.

A further problem with known endotracheal tubes, and in particular, endotracheal tubes which are adapted for manually inflating with a syringe, or indeed, are adapted for inflating by a compressed air source is that a check valve is required in the communicating tube to the cuff for maintaining the cuff inflated after it has been disconnected from the syringe or compressed air source.

Attempts to overcome these problems associated with endotracheal tubes have been made. In particular, attempts have been made to provide apparatus for varying the cuff pressure as the pressure of the ventilating medium varies, in other words to provide high cuff pressure during the inspiratory phase of each breathing cycle and low cuff pressure during the expiratory phase. In general, such apparatus require that the cuff be inflated from an external source, typically an external compressed air source, such as a compressed air source available in a hospital. This, thus requires that the endotracheal tube as well as being connected to a ventilator must also be connected to a separate compressed air source, and in the absence of such a compressed air source the endotracheal tube must be connected to a large pressurised gas cylinder, or alternatively the endotracheal tube cannot be used. A valving system which generally includes solenoid operated valves and a pressure regulating system are also required for controlling and regulating the pressure of the air or gas from the external source for supply to the cuff. Such systems suffer from the disadvantage that they are slow to react, and in general are unable to accurately. track transitions between the inspiratory and expiratory phases of breathing cycles.

U.S. Pat. No. 4,825,862 of Sato discloses apparatus for regulating cuff pressure in an endotracheal tube. The apparatus comprises a pressure regulator for regulating the pressure of a separate gas supply to the cuff in response to pressure variation in breathing cycles. However, the regulator disclosed in this U.S. specification is a mechanically operated regulator, and in general, would be relatively slow to react, and in general, would be unable to react with the speed required to vary the pressure during individual breathing cycles. However, irrespective of whether the regulator of the apparatus of Sato would be capable of tracking the pressure variation of the ventilating medium during each breathing cycle, the apparatus of Sato requires a separate gas supply, in other words, the apparatus of Sato would have to be connected to an external gas supply, for example, a hospital compressed air system or other such external source.

U.S. Pat. No. 5,235,973 of Levin son also discloses a cuff pressure controller for controlling cuff pressure of an endotracheal tube in which the cuff pressure is held at a high pressure during the inspiratory phase of a breathing cycle, and is held at low pressure during the expiratory phase. However, the cuff pressure controller of Levinson requires the supply of gas from a separate external gas source for inflating the cuff of the endotracheal tube. Additionally, pressure control valves for controlling the pressure of the gas supply to the cuff are also required.

Accordingly, there is therefore a need for apparatus for controlling cuff pressure of an endotracheal tube for minimising leak past of ventilating medium into the mouth of the subject during the inspiratory phase of a breathing cycle, and which avoids the need for having a separate external pressurised gas source for inflating the cuff.

The present invention is directed towards providing such apparatus.

According to the invention there is provided apparatus for controlling cuff pressure in a cuff of an endotracheal tube, the apparatus comprising a control means for controlling the pressure of an inflating medium for inflating the cuff at respective first and second pressure levels during the inspiratory and expiratory phases, respectively of each breathing cycle of a subject, wherein the apparatus comprises an inflating medium supply means for supplying inflating medium to the cuff, and the control means controls the inflating medium supply means for supplying the inflating medium at the second pressure level to the cuff during the expiratory phase of each breathing cycle.

In one embodiment of the invention the inflating medium supply means is a variable pressure inflating medium supply means.

In another embodiment of the invention the control means controls the inflating medium supply means for supplying the inflating medium at the first pressure level to the cuff during the inspiratory phase of each breathing cycle.

In another embodiment of the invention a monitoring means is provided for determining the transitions between the respective inspiratory and expiratory phases during a series of sequential breathing cycles, and the control means is responsive to the monitoring means for controlling the inflating medium supply means for supplying the inflating medium to the cuff at the respective first and second pressure levels during the inspiratory and expiratory phases, respectively, of each breathing cycle.

Preferably, the monitoring means monitors the pressure of the ventilating medium to the subject, and the control means is responsive to the monitoring means for controlling the inflating medium supply means for supplying the inflating medium at the first pressure level as a function of the pressure of the ventilating medium during the inspiratory phase of each breathing cycle.

Advantageously, the control means controls the inflating medium supply means for supplying the inflating medium at the first pressure level tracking the pressure of the ventilating medium during the inspiratory phase of each breathing cycle.

In one embodiment of the invention the control means controls the inflating medium supply means for supplying the inflating medium at the first pressure level similar to the pressure of the ventilating medium during the inspiratory phase of each breathing cycle.

In another embodiment of the invention the control means controls the inflating medium supply means for supplying the inflating medium at the first pressure level at a pressure differential relative to the pressure of the ventilating medium during the inspiratory phase of each breathing cycle.

In a further embodiment of the invention the control means controls the inflating medium supply means for supplying the inflating medium at the first pressure level at a predetermined pressure above the pressure of the ventilating medium during the inspiratory phase of each breathing cycle. Preferably, the predetermined pressure by which the first pressure level of the inflating medium is above the pressure of the ventilating medium during the inspiratory phase of each breathing cycles lies in the range of 1 mBar to 10 mBar. Advantageously, the predetermined pressure by which the first pressure level of the inflating medium is above the pressure of the ventilating medium during the inspiratory phase of each breathing cycle lies in the range of 2 mBar to 3 mBar.

In another embodiment of the invention the control means controls the inflating medium supply means for supplying the inflating medium at the first pressure level at a predetermined pressure below the pressure of the ventilating medium during the inspiratory phase of each breathing cycle. Preferably, the predetermined pressure by which the first pressure level of the inflating medium is below the pressure of the ventilating medium during the inspiratory phase of each breathing cycle lies in the range of 5 mBar to 20 mBar.

In an alternative embodiment of the invention the control means controls the inflating medium supply means for supplying the inflating medium at the first pressure level at a constant predetermined first pressure level.

In one embodiment of the invention the monitoring means monitors the pressure of the ventilating medium in the endotracheal tube. Advantageously, the monitoring means comprises a pressure transducer, and preferably, the ventilating medium is teed off from the endotracheal tube to the monitoring means.

In one embodiment of the invention the medium for inflating the cuff at the first pressure level during the inspiratory phase of each breathing cycle is derived from the ventilating medium. Advantageously, the ventilating medium is derived from the endotracheal tube. Preferably, the control means comprises a valving means for supplying medium to the cuff for inflating thereof, the medium being derived from the ventilating medium and the inflating medium supply means during the inspiratory phase of each breathing cycle, and from the inflating medium supply means during the expiratory phase of each breathing cycle. Advantageously, the valving means comprises a means for valving the medium of highest pressure of the inflating medium and the ventilating medium to the cuff. Ideally, the valving means comprises a pair of one way valves connected respectively to the inflating medium supply means and to the endotracheal tube for supplying the inflating medium from the inflating medium supply means and the ventilating medium from the endotracheal tube to the cuff.

In one embodiment of the invention the control means controls the inflating medium supply means for supplying the inflating medium at the second pressure level at a second predetermined pressure level.

In another embodiment of the invention the control means controls the inflating medium supply means for supplying the inflating medium at the second pressure level at a predetermined pressure below the pressure of the ventilating medium during the inspiratory phase of each breathing cycle.

In a further embodiment of the invention the control means controls the inflating medium supply means for supplying the inflating medium at the second pressure level at a predetermined constant pressure.

Preferably, the second pressure level is less than the first pressure level.

In one embodiment of the invention the inflating medium supply means comprises an inflating medium supply pump. Preferably, the inflating medium supply pump is provided by an electric motor operated pump. Advantageously, the electric motor of the inflating medium supply pump is controlled by the control means.

Preferably, a smoothing means is provided for smoothing the pressure of the inflating medium from the inflating medium supply means. Advantageously, the smoothing means comprises a reservoir defining a buffering chamber for buffering the inflating medium.

In one embodiment of the invention a pressure reducing means is provided for reducing the pressure in the cuff as each breathing cycle is transitioning from the inspiratory to the expiratory phase. Preferably, the pressure reducing means comprises an exhaust vent from the smoothing means, the exhaust vent being of relatively small bore size such as not to significantly affect the pressure of the inflating medium at which the inflating medium is being supplied to the cuff.

In one embodiment of the invention an input means is provided for facilitating inputting of a command to the control means relating to the first and second pressure levels. Advantageously, the input means comprises an input keypad.

Preferably, the control means comprises a microcontroller.

In a preferred embodiment of the invention the apparatus comprises a housing, and the inflating medium supply means and the control means are located within the housing. Preferably, the monitoring means is located within the housing. Advantageously, the smoothing means is located within the housing. Preferably, the input means is located in the housing and is externally accessible. Ideally, toe housing is adapted for pole mounting on or beside a bed of a subject In an alternative embodiment of the invention the apparatus is adapted for mounting in a ventilator supplying the ventilating medium, and preferably, the apparatus is responsive to the ventilator transitioning between the respective inspiratory and expiratory phases of the breathing cycle.

In a further embodiment of the invention the apparatus also comprises an endotracheal tube. Ideally, a bleed off means is provided from the endotracheal tube for bleeding off ventilating medium from the endotracheal tube to the valving means and/or the monitoring means.

In one embodiment of the invention a communicating means is provided from the endotracheal tube for communicating with the inflating medium supply means.

In a further embodiment of the invention the endotracheal tube terminates at the end opposite the cliff in a coupling for coupling the endotracheal tube to a ventilating medium supply source.

In a still further embodiment of the invention the endotracheal tube comprises an adapter for facilitating connection of the delivery means and the connecting means to the endotracheal tube.

The advantages of the invention are many. Two important advantages of the invention are firstly, that the apparatus allows the pressure to which the cuff is inflated to track in real time the pressure of the ventilating medium, and secondly, the apparatus provides for a reduction in the pressure to which the cuff is inflated during the expiratory phase of each breathing cycle, thereby reducing discomfort to the subject, and also avoiding damage to the trachea and its related organs. Furthermore, use of the apparatus according to the invention allows an endotracheal tube to be used without the need for an additional external source of pressurised gas for inflating the cuff of an endotracheal tube. The provision of the inflating medium supply means in the apparatus according to the invention supplies the inflating medium directly to the cuff. Additionally, by providing the inflating medium supply means in the apparatus a relatively simple apparatus is provided, and the inflating medium can be supplied to the cuff without the need for complex solenoid operated valving systems, and without the need for a complex pressure regulating valving system. Additionally, by virtue of the fact that the inflating medium is directly supplied by the inflating medium supply means in response to the monitored pressure of the ventilating medium the apparatus responds relatively quickly to the transition between the inspiratory and expiratory phases of each breathing cycle, and between the expiratory and inspiratory phases of sequential breathing cycles. The provision of the inflating medium supply means as an electrically powered pump provides a particularly efficient and quick to respond apparatus, and providing the control means as a microcontroller further enhances the response time of the apparatus for supplying the inflating medium at the respective first and second pressure levels in response to transitions between the inspiratory and expiratory phases of each breathing cycle.

Furthermore, by virtue of the fact that the cuff is continuously inflated, the need for a check valve for preventing deflation of the cuff is no longer required. By virtue of the fact that the cuff is continuously inflated there is no need for the cuff to be provided by a highly compliant material such as a latex material, the cuff may be provided by any suitable inflatable material, and typically, would be of a plastics material. This, thus, allows the endotracheal tube to be provided without the need for a latex material thus avoiding any danger of allergic reactions in a subject. Furthermore, since the cuff is continuously inflated the leaking of anaesthetic gases into the cuff has no effect on the inflating of the cuff, and furthermore, even if the cuff is of a material which is permeable to any of the anaesthetic gases, or indeed any other media being supplied to the subject there is no danger of over-inflating of the cuff. Additionally, the fact that the cuff may be provided in a less compliant material also reduces any danger of over-inflating of the cuff.

A further advantage of the invention is that it provides a relatively simple control apparatus for controlling cuff pressure at two levels, thereby allowing the cuff pressure to be relaxed to the lower second pressure level during the expiratory phase of the breathing cycle and raised to the higher first pressure level for minimising leakage of the ventilating medium into the mouth of the subject during the inspiratory phase of the breathing cycle.

The invention will be more clearly understood from the following description of some preferred embodiments thereof which are given by way of example only with reference to the accompanying drawings in which.

Figure 1:
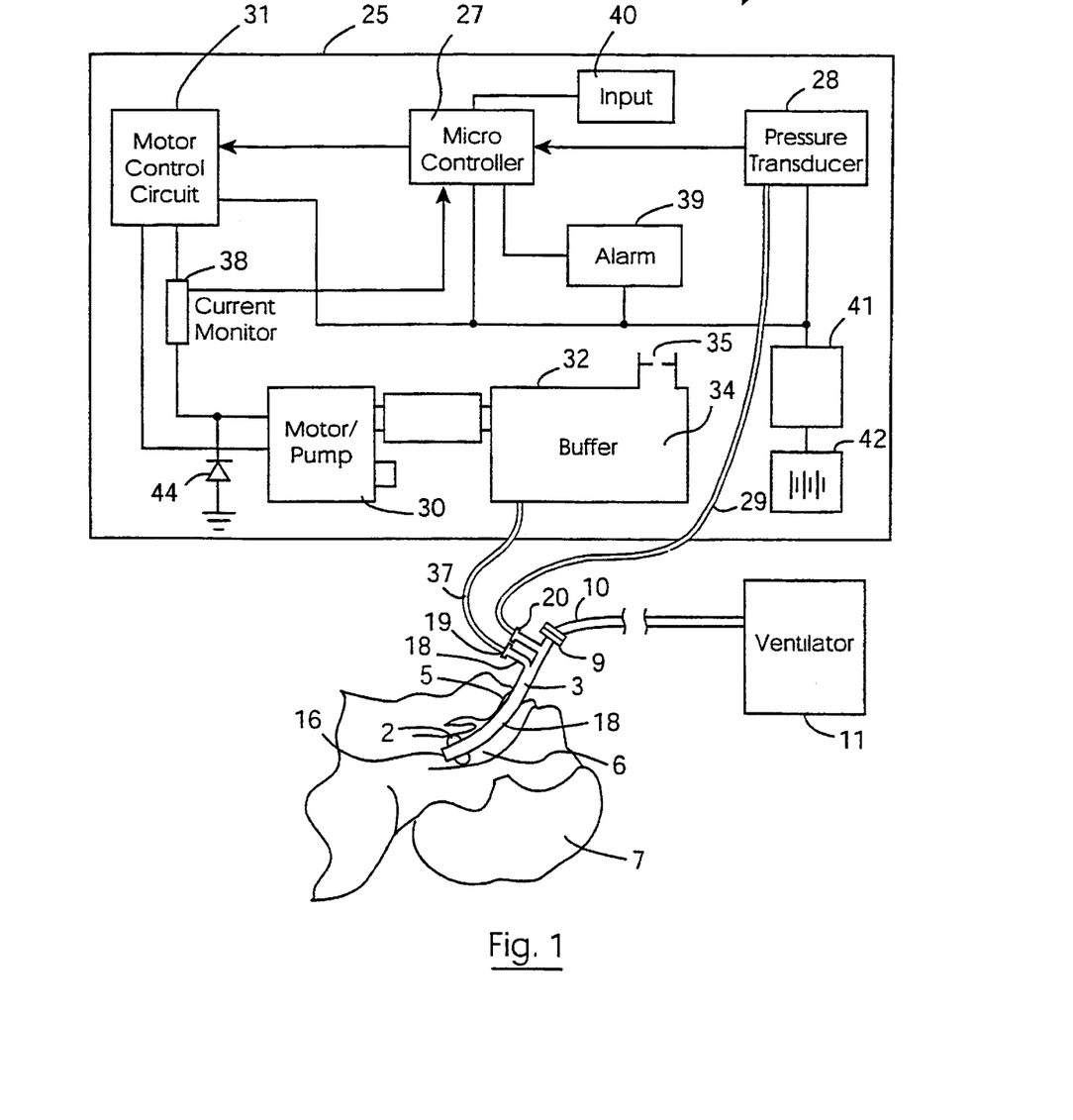
FIG. 1 is a partly diagrammatic block representation of apparatus according to the invention for controlling cuff pressure in an endotracheal tube.
Figure 2:
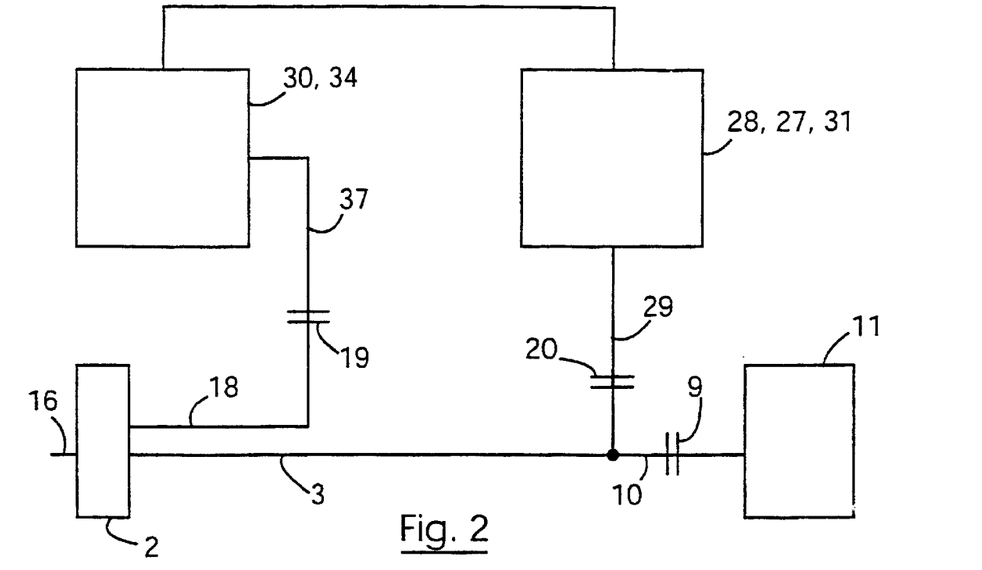
FIG. 2 is a circuit diagram of the apparatus of FIG. 1.

Referring to the drawings and initially to FIGS. 1 and 2 there is illustrated apparatus according to the invention indicated generally by the reference numeral 1 for controlling cuff pressure in an inflatable cuff 2 of an endotracheal tube 3. Such endotracheal tubes 3 will be well known to those skilled in the art and are used for ventilating a subject, typically, a subjects in a prone condition. The endotracheal tube 3 is inserted through the mouth 5 into the trachea 6 of a subject 7, and a coupling 9 on one end of the endotracheal tube 3 is provided for connecting the endotracheal tube 3 to a supply tube 10 for in turn, connecting to a ventilator 11. Ventilating medium is supplied to the subject from the ventilator 11.

The cuff 2 extends around an end 16 of the endotracheal tube 3 which is inserted in the trachea 6, and is inflated for sealing the endotracheal tube 3 in the trachea 6 for preventing leak past of ventilating medium into the mouth of the subject during the inspiratory phase of each breathing cycle. A communicating tube 18 extends along part of the endotracheal tube 3, and is integrally formed therewith for communicating with the cuff 2 for inflating thereof. The communicating tube 18 terminates in a connector 19 for connecting the communicating tube 18 and in turn the cuff 2 to the apparatus 1 as will be described below. A tee connector 20 is teed off from the endotracheal tube 3 and communicates with the ventilating medium in the endotracheal tube 3 for connecting the apparatus 1 to the ventilating medium as will be described below.

The apparatus 1 comprises a housing 25 which is illustrated in block representation only in FIG. 1. The housing 25 is suitable for pole mounting on a pole extending upwardly from a bed of a subject, or located adjacent the bed of a subject. A control means comprising a microcontroller 27 is located in the housing 25 and controls the operation of the apparatus 1. A monitoring means comprises a pressure transducer 28 located in the housing 25, which is connected by a connecting tube 29 to the tee connector 20 monitors the pressure of the ventilating medium in the endotracheal tube 3. The microcontroller 27 reads the output from the pressure transducer 28 for determining the pressure of the ventilating medium in the endotracheal tube 3, and also for determining transitions between the inspiratory phase and the expiratory phase of each breathing cycle and vice versa.

An inflating medium supply means comprising a DC electric motor driven variable pressure supply pump 30 is located in the housing 25 and is operated under the control of a motor control circuit 31 by the microcontroller 27 for supplying inflating medium, which in this embodiment of the invention is air at two pressure levels, namely, a first pressure level during the inspiratory phase of each breathing cycle, and a second pressure level which is lower than the first pressure level during the expiratory phase of each breathing cycle.

A smoothing means comprising a reservoir 32 which forms a buffer chamber 34 receives the inflating medium from the supply pump 30 for smoothing out pump induced pressure variations. The reservoir 32 is located in the housing 25. A pressure reducing means comprising an exhaust vent 35 extends from the buffer chamber 34 for facilitating exhausting of inflating medium for reducing the pressure in the cuff 2 as the breathing cycle is transitioning from the inspiratory phase to the expiratory phase. The exhaust vent 35 is of relatively small bore size, and the bore sizes is such that it does not lead to pressure loss from the buffer chamber 34 while the pressure of the inflating medium is being supplied by the supply pump 30 at the respective first and second pressure levels. A delivery means, namely, a delivery tube 37 extends from the buffer chamber 34 to the connector 19 for delivering inflating medium to the cuff 2 at the respective first and second pressure levels during the inspiratory and expiratory phases, respectively, of each breathing cycle.

The motor control circuit 31 is located in the housing 25, and a current monitor 38 also located in the housing 25 monitors the output current from the motor control circuit 31. The output from the current monitor 38 is read by the microcontroller 27 for detecting any danger of the supply pump 30 operating at a level which would cause the inflating medium to be supplied at respective pressures above the respective first and second pressure levels. An alarm means comprising an alarm circuit 39 is operable under the control of the microcontroller 27 in response to an over pressure being determined from signals read by the microcontroller 27 from the current monitor 38. Thee alarm circuit 39 may comprise an audio or visual alarm, for example, a siren or a light emitting diode which would give either an audible or visual indication of an over pressure condition existing.

An input means comprising an input keypad 40 is provided on the housing 25 for facilitating inputting of commands to the microcontroller 27 for setting the first and second pressure levels as will be described below. As power supply circuit 41 located in the housing 25 is adapted for connecting to an AC mains electricity power supply for powering the apparatus 1. A battery back up power supply circuit 42 also located in the housing 25 provides battery back up to the apparatus 1 in the event of a power supply failure. A zener diode 44 clamps one of the power supply inputs to the motor of the supply pump 30 to ground for avoiding an over voltage condition.

The microcontroller 27 may be programmed for controlling the power supply to the pump motor for in turn controlling the rate at which the supply pump 30 supplies the inflating medium so that the inflating medium may be supplied at various. arrangements of first and second pressure levels. At its simplest, the microcontroller 27 may be programmed for controlling the supply pump 30 for supplying the inflating medium at the first pressure level which would be a constant pressure level, and for supplying the inflating medium at the second pressure level which would also be a constant pressure level, but which would be less than the constant first pressure 30 level. The respective values of the desired first and second constant pressure levels would be entered through the keypad 40. Typically, the first pressure level would ideally be selected to be similar to the highest pressure to which the ventilating medium would be expected to rise during the inspiratory phase of each breathing cycle. The second pressure level would be a pressure level sufficient for securing and retaining the endotracheal tube 3 in the trachea 6.

Alternatively, the microcontroller 27 may be programmed for allowing the first pressure level to be a varying pressure level which would track the pressure of the ventilating medium during the inspiratory phase of the breathing cycle. The first pressure level could track the monitored ventilating medium pressure identically, or could track the ventilating medium pressure at a pressure above or below the ventilating medium pressure. In this case the microcontroller 27 would control the supply pump to supply the inflating medium at the first pressure level in response to the pressure of the ventilating medium read from the pressure transducer 28. Where the first pressure level is tracking the pressure of the ventilating medium at a pressure above or below the pressure of the ventilating medium, it is envisaged that the pressure differential between the first pressure level and the ventilating medium pressure would be relatively slight. Similarly in the case of the second pressure level, the microcontroller 27 could be programmed for operating the supply pump 30 for supplying the inflating medium at the second pressure level which would vary during the expiratory phase of each breathing cycle, and would track the pressure of the ventilating medium during the expiratory phase of the breathing cycle at an identical pressure to the ventilating medium pressure or at a pressure slightly above or below that of the ventilating medium during the expiratory phase. Although, in general, it is believed that it would be preferable to maintain the second pressure level at a predetermined constant pressure. If the microcontroller 27 were programmed for operating the supply pump 30 for supplying the inflating medium at the first and/or second pressure levels tracking the ventilating medium pressure at predetermined pressure differentials, then the difference between the ventilating medium pressure and the first and second pressure levels at which the first and second pressure levels are to track the ventilating medium pressure would be entered through the input keypad 40.

Additionally, the microcontroller 27 may be programmed to adjust the rate of change of the pressure of the inflating medium when transitioning between the first and second pressure levels, and in particular, when transitioning from the second pressure level to the first pressure level to avoid discomfort to the subject.

In use, the endotracheal tube 3 is inserted through the mouth 5 of the subject 7 into the trachea 6, and is connected to a ventilator 11 by coupling the supply tube 10 from the ventilator 11 to the coupling 9. With the apparatus 1 pole mounted adjacent the subject the connecting tube 29 is connected to the teed connector 20 for communicating the pressure transducer 28 with the ventilating medium in the endotracheal tube 3. The delivery tube 37 is connected to the connector 19 for supplying the inflating medium to the cuff 2. The desired values or differential values to of the first and second pressure levels to which the cuff 2 is to be inflated during the inspiratory and expiratory phases, respectively, of each breathing cycle are inputted to the microcontroller 27 through the input keypad 40, or alternatively, the desired values of the first and second pressure levels are inputted through the keypad 40. The apparatus is now ready for use, and as the subject is ventilated the is microcontroller 27 operates the supply pump 30 through the motor control circuit 31 for continuously supplying inflating medium at the first pressure level during the inspiratory phase of each breathing cycle, and for continuously supplying the inflating medium for inflating the cuff 2 at the second pressure level during the expiratory phase of each breathing cycle. The microcontroller 27 reads the output from the pressure transducer 28 for determining the ends of the respective inspiratory and expiratory phases of each breathing cycle, and as the inspiratory phase of the breathing cycle is just about to end the microcontroller 27 controls the supply pump 30 through the motor control circuit 31 for switching from supplying inflating medium at the first pressure level to supplying the inflating medium at the second pressure level. Similarly, as the microcontroller 27 determines from the output from the pressure transducer 28 that the expiratory phase of each breathing cycle is just about to end the microcontroller 27 operates the supply pump 30 through the motor control circuit 31 for switching over to supply the inflating medium at the first pressure level, and so operation of the apparatus 1 continues and alternately cycles between supplying inflating medium to the cuff 2 at the first and second pressure levels during the inspiratory and expiratory phases, respectively, of each breathing cycle.

Figure 3:
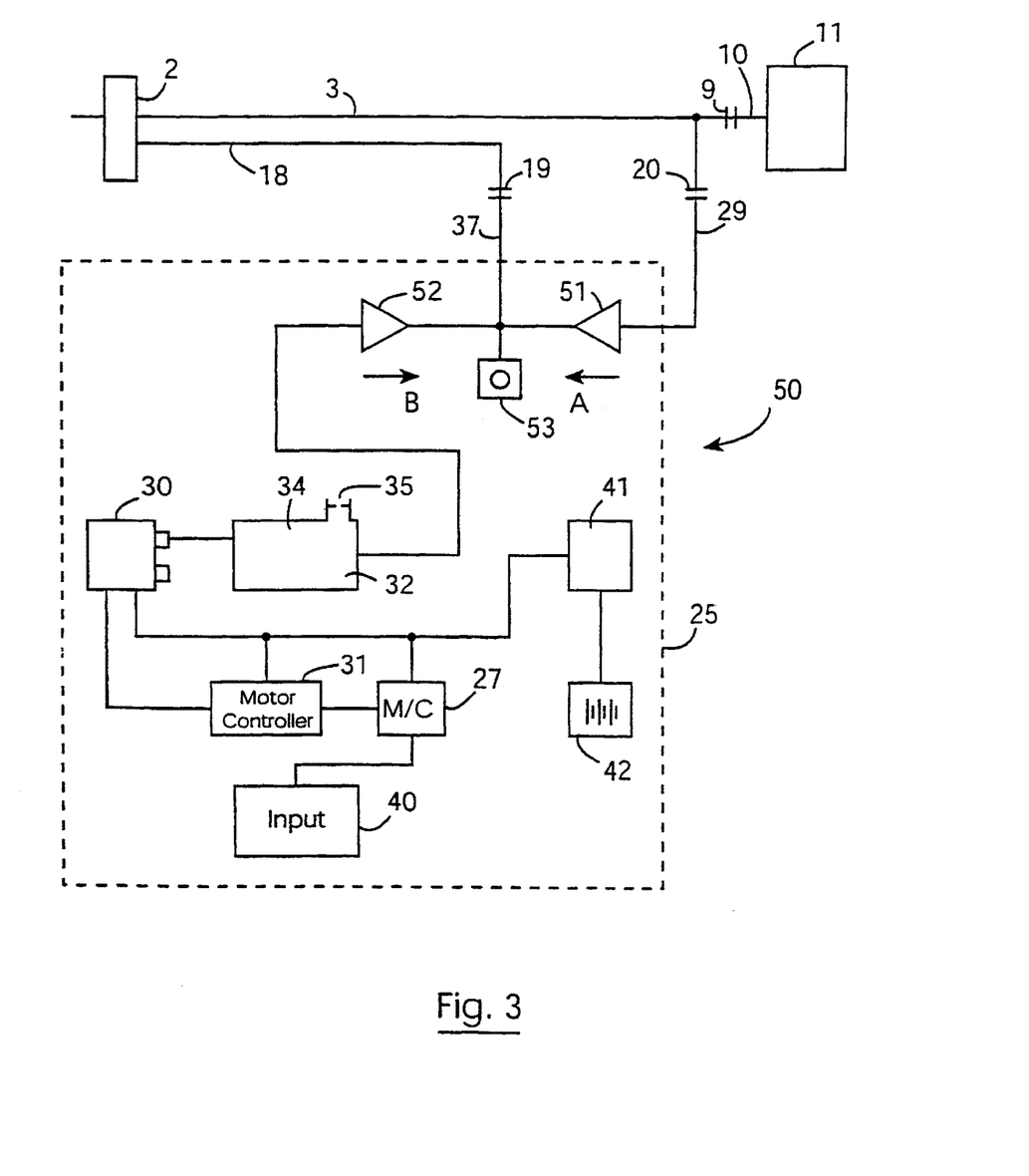
FIG. 3 is a circuit diagram of apparatus according to another embodiment of the invention for controlling cuff pressure in an endotracheal tube.

Referring now to FIG. 3 there is illustrated apparatus according to another embodiment of the invention indicated generally by the reference numeral 50 also for controlling cuff pressure in an endotracheal tube. The apparatus 50 is somewhat similar to the apparatus 1, and similar components are identified by the same reference numerals. In this embodiment of the invention the apparatus 50 also comprises a housing 25, similar to the housing 25 of the apparatus 1. The supply pump 30 operated under the control of the motor control circuit 31 is also located in the housing 25 for supplying inflating medium to the cuff 2 through the buffer chamber 34. In this embodiment of the invention the microcontroller 27 controls the supply pump 30 through the motor control circuit 31 for supplying the inflating medium at only one pressure level, which in this embodiment of the invention is the second pressure level. The second pressure level is higher than the pressure of the ventilating medium during the expiratory phase, and is less than the pressure of the ventilating medium during the inspiratory phase of each breathing cycle, but is sufficient for maintaining the cuff 2 inflated for securing the endotracheal tube 3 in the trachea 6 during the expiratory phase of each breathing cycle.

In this embodiment of the invention a pressure transducer is not provided. However, the connecting tube 29 instead of being connected to a pressure transducer is connected through a valving means along with the output from the buffer chamber 34 to the delivery tube 37. The valving means, which in this embodiment of the invention forms part of the control means comprises a pair of one way valves 51 and 52 which are one way In the directions of the arrows A and B, respectively and are arranged so that the medium of the inflating medium and the ventilating medium of highest pressure is supplied to the cuff 2 for inflating thereof. The one way valve 51 connects the connecting tube 29 to the delivery tube 37 for supplying the ventilating medium which is bled-off from the endotracheal tube 3 to the cuff 2. The one way valve 52 connects the buffer chamber 34 to the delivery tube 37 for supplying the inflating medium from the buffer chamber 34 to the cuff 2. Accordingly, since during the inspiratory phase of each breathing cycle the pressure of the ventilating medium is higher than its pressure during the expiratory phase, and additionally, since the supply pump 30 is controlled to supply inflating medium at the second pressure level which is lower than the pressure of the ventilating medium during the inspiratory phase of each breathing cycle, the cuff 2 is inflated largely by the ventilating medium through the connecting tube 29, the one way valve 51 and the delivery tube 37 during the inspiratory phase of each breathing cycle, although inflating medium from the supply pump 30 does contribute to inflating of the cuff 2 during the inspiratory phase of each breathing cycle. However, since the second pressure level at which the inflating medium is being supplied by the supply pump 30 is higher than the pressure of the ventilating medium during the expiratory phase of each breathing cycle, the cuff 2 is inflated by the inflating medium from the supply pump during the expiratory phase of each breathing cycle. A pressure reducing means, which is similar to the pressure reducing means attached to the buffer chamber 34 is provided by an exhaust vent 53 and is connected to the delivery tube 37 at the connection of the one way valves 51 and 52 for facilitating reducing the pressure in the cuff 2 during the transition from the inspiratory to the expiratory phase of each breathing cycle. The exhaust vent 53 is of sufficiently small bore to avoid loss in pressure to the cuff 2 during the inspiratory and expiratory phases of the breathing cycle, but is of sufficient site for reducing the pressure in the cuff 2 as required during the expiratory phase of each breathing cycle.

In use, the endotracheal tube 3 is inserted in the trachea of the subject as already described, and is connected to the apparatus 50 so that the connecting tube 29 connects the tee connector 20 to the one way valve 51, and the delivery tube 37 connects the connector 19 of the communicating tube 18 to the one way valve 52. The desired value of the second pressure level is entered through the input keypad 40, and the endotracheal tube 3 is connected to a ventilator 11 through the supply tube 10. The apparatus 50 is now ready for use, and the microcontroller 27 controls the supply pump 30 through the motor control circuit 31 for continuously supplying inflating medium at the second pressure level. The cuff 2 is thus inflated during the inspiratory and expiratory phases of the breathing cycle by ventilating medium through the one way valve 51 and by the inflating medium from the supply pump 30 through the one way valve 52.

Figure 4:
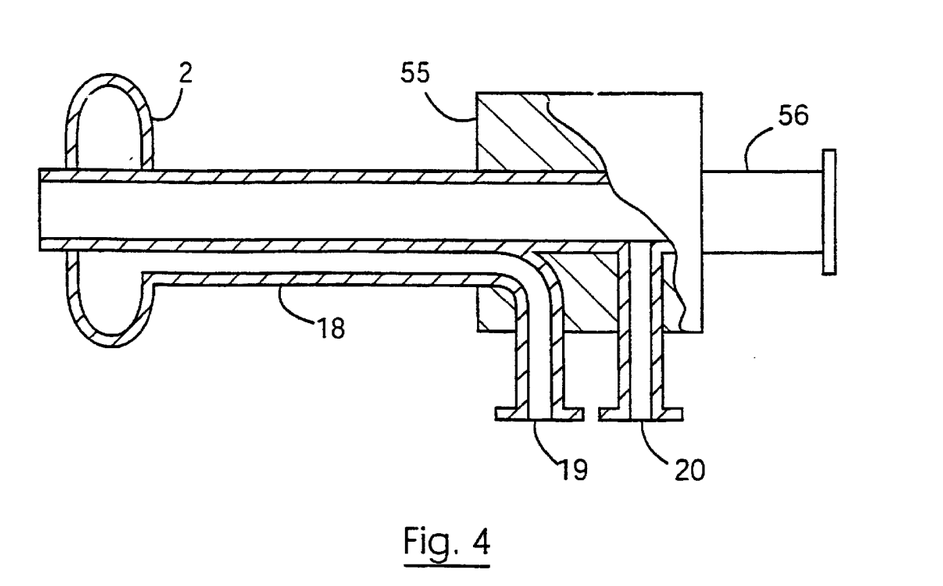
FIG. 4 is a partly cross-sectional view of an endotracheal tube for use with the apparatus of FIGS. 1 to 3.

Referring now to FIG. 4 there is illustrated an endotracheal tube 56 also according to the invention. An adapter 55 is located on the endotracheal tube 56, which incorporates two connectors, namely, the connector 19 to the communicating tube 18, and the teed connector 20 for bleeding off the ventilating medium from the endotracheal tube 56. The advantage of providing the adapter 55 as a single unit is that it facilitates connection of both the apparatus 1 and 50 to the endotracheal tube.

While the valving means of the apparatus 50 has been described as comprising a pair of one way valves, it is envisaged that any other suitable valving means may be provided, and it is envisaged that solenoid valves may be provided which would be operated under the control of the microcontroller. However, in such a case, a monitoring means would be provided for determining the transitions from the inspiratory to the expiratory phases and vice versa of the breathing cycles. Such a monitoring means would be provided in the same fashion as the monitoring means While the monitoring means for detecting the transition between the inspiratory and expiratory phases of a breathing cycle has been described as comprising a pressure transducer, it will be readily apparent to those skilled in the art that any other suitable monitoring means for detecting transition between the inspiratory and expiratory phases of each breathing cycle may be used. For example, it is envisaged that a flow sensing means may be provided for sensing the direction of flow of the ventilating medium in the endotracheal tube, and a reversal of the direction of flow of the ventilating medium would indicate a transition from the inspiratory to the expiratory phases of each breathing cycle. Needless to say, any other suitable pressure sensing means may be used or any other type of flow sensing means may be used.

It is also envisaged that the transition between the inspiratory and expiratory phases of each breathing cycle could be communicated to the control means directly from the ventilator supplying the ventilating medium. In which case it is envisaged that a signal would be relayed or transmitted from the ventilator to the control means indicating each transition, and the control means would be responsive to the signal from the ventilator for controlling the inflating medium supply means. It is also envisaged that the apparatus 1 and 50 could be located in a ventilator supplying the ventilating medium, and in which case a separate supply line would supply the inflating medium from the apparatus to the cuff. Additionally, in the event that the apparatus were located in the ventilator, it is also envisaged that the monitoring means could be dispensed with, and the apparatus could share the microcontroller of the ventilator. In which case, the supply pump could be operated under the control of the ventilator microcontroller for supplying the ventilating medium at the respective first and second pressure levels or at the second pressure level as appropriate.

It is also envisaged that suitable filters may be provided for filtering the supplies of the inflating medium and the ventilating medium to and from the apparatus.

It will be appreciated that the provision of the adapter 55 in the endotracheal tube 56 provides a relatively simple, neat and convenient arrangement for connecting the apparatus 1 and 50 to the endotracheal tube. In general, when the means for detecting the transition between the inspiratory and expiratory phases of a breathing cycle is provided by a pressure sensor, it is desirable that the pressure of the ventilating medium be monitored as closely as possible to the subject, and thus, the adapter 55 may be located on the endotracheal tube relatively close to the mouth of the subject. Needless to say, if the means for determining the transition between the inspiratory and expiratory phases of a breathing cycle were provided by a flow sensor, it is also desirable that the flow of the ventilating medium be monitored as closely as possible to the mouth of the subject.

What is claimed is:

1. An apparatus for supplying an inflating medium to a cuff of an endotracheal tube and for controlling a pressure of the inflating medium in the cuff, the apparatus comprising:
   an inflating medium supply means for supplying the inflating medium to the cuff for inflating thereof;
   a control means for controlling the pressure of the inflating medium being supplied to the cuff at a first pressure level and a second pressure level during an inspiratory and an expiratory phase, respectively, of each breathing cycle of a subject, the inflating medium for inflating the cuff being derived from a ventilating medium being supplied to the subject, and from the inflating medium supply means; and
   the control means further comprising a valving means for supplying inflating medium to the cuff for inflating thereof, the valving means deriving the inflating medium from the ventilating medium and the inflating medium supply means during the inspiratory phase of each breathing cycle of the subject, and from the inflating medium supply means during the expiratory phase of each breathing cycle.

2. The apparatus of claim 1 wherein the valving means further comprises a means for supplying whichever of the inflating medium and the ventilating medium is at the highest pressure to the cuff.

3. The apparatus of claim 1 wherein the valving means further comprises a pair of one way valves connected respectively to the inflating medium supply means and a ventilating medium supply for supplying inflating medium from the inflating medium supply means and the ventilating medium to the cuff.

4. The apparatus of claim 1 wherein the control means controls the inflating medium supply means for supplying the inflating medium at the second pressure level at a predetermined pressure level.

5. The apparatus of claim 4 wherein the control means controls the inflating medium supply means for supplying the inflating medium at the second pressure level at a predetermined pressure level below the pressure of the ventilating medium during the inspiratory phase of each breathing cycle.

6. The apparatus of claim 4 wherein the control means controls the inflating medium supply means for supplying the inflating medium at the second pressure level at a second predetermined constant pressure.

7. The apparatus of claim 1 wherein the second pressure level is less than the first pressure level.

8. The apparatus of claim 1 wherein the inflating medium supply means a variable pressure inflating medium supply means.

9. The apparatus of claim 1 wherein the inflating medium supply means comprises an inflating medium supply pump.

10. The apparatus of claim 9 wherein the inflating medium supply pump is an electric motor operated pump, the electric motor being controlled by the control means.

11. The apparatus of claim 1 wherein a smoothing means is provided for smoothing the pressure of the inflating medium from the inflating medium supply means.

12. The apparatus of claim 11 wherein the smoothing means comprises a reservoir defining a buffering chamber for buffering the inflating medium.

13. The apparatus of claim 11 wherein a pressure reducing means is provided for reducing the pressure in the cuff as each breathing cycle is transitioning from the inspiratory to the expiratory phase, the pressure reducing means comprising an exhaust vent from the smoothing means, the exhaust vent being of relatively small bore size such as not to significantly affect the pressure of the inflating medium at which the inflating medium is being supplied to the cuff.

14. The apparatus of claim 1 wherein the apparatus further comprises a housing, and one or more of the inflating medium supply means, the control means, or a smoothing means are located within the housing.

15. The apparatus of claim 14 wherein the housing is adapted for pole mounting on or beside a bed of a subject.

16. The apparatus of claim 1 wherein the apparatus is adapted for mounting in a ventilator supplying the ventilating medium, and is responsive to the ventilator transitioning between the respective inspiratory and expiratory phases of the breathing cycle.

17. The apparatus of claim 1 wherein the apparatus further comprises an endotracheal tube, and a bleed off means is provided from the endotracheal tube for bleeding off ventilating medium from the endotracheal tube to the valving means.

18. The apparatus of claim 17 wherein a connecting means is provided from the endotracheal tube for communicating with the valving means, and a delivery means is provided from the valving means for connection to the cuff.

19. The apparatus of claim 1 wherein the valving means during the inspiratory phase of each breathing cycle, derives inflating medium for inflating the cuff largely from the ventilating medium with a contribution from the inflating medium supply means.

* * * * *